United States Patent [19]

Ondetti

[11] 4,282,235
[45] Aug. 4, 1981

[54] DERIVATIVES OF THIAZOLIDINECARBOXYLIC ACIDS AND RELATED ACIDS

[75] Inventor: Miguel A. Ondetti, Princeton, N.J.

[73] Assignee: E. R. Squibb & Sons, Inc., Princeton, N.J.

[21] Appl. No.: 79,284

[22] Filed: Sep. 27, 1979

Related U.S. Application Data

[60] Division of Ser. No. 907,452, May 22, 1978, Pat. No. 4,192,878, which is a continuation-in-part of Ser. No. 836,107, Sep. 23, 1977, abandoned, which is a continuation-in-part of Ser. No. 747,281, Dec. 3, 1976, abandoned.

[51] Int. Cl.³ .............................................. C07D 277/02
[52] U.S. Cl. ..................... 424/270; 548/201; 548/200
[58] Field of Search ................. 548/200, 201; 424/270

[56] References Cited

U.S. PATENT DOCUMENTS

| | | | |
|---|---|---|---|
| 3,886,149 | 5/1975 | Treuner et al. | 260/243 C |
| 3,920,639 | 11/1975 | Dolfini | 260/243 C |
| 4,046,889 | 9/1977 | Ondetti et al. | 424/244 |
| 4,192,878 | 3/1980 | Ondetti | 424/270 |

FOREIGN PATENT DOCUMENTS 2138121 2/1973 Fed. Rep. of Germany.

OTHER PUBLICATIONS

Rosamond et al., Journ. Med. Chem. 19, 873–876 (1976).
CA 72, 337, (1970), 31780v.
Japanese Jour. of Pharmacology, 28 suppl. 107P (1978).
Chem. Pharm. Bull. 26(4) 1333–1335 (1978).
Internal Report of E. R. Squibb & Sons, Inc., Presentation by Ohya et al., at 90th Meeting of Pharmaceutical Society of Japan held 4-4-78 in Japan.

*Primary Examiner*—Nicholas S. Rizzo
*Attorney, Agent, or Firm*—Lawrence S. Levinson; Donald J. Barrack

[57] ABSTRACT

New substituted derivatives of thiazolidine-, thiazane and related carboxylic acids which have the general formula

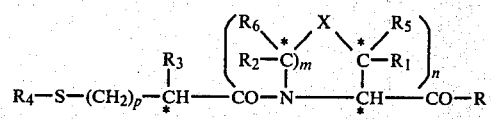

are useful as angiotensin converting enzyme inhibitors.

13 Claims, No Drawings

DERIVATIVES OF THIAZOLIDINECARBOXYLIC ACIDS AND RELATED ACIDS

This is a division of application Ser. No. 907,452, filed May 22, 1978, now U.S. Pat. No. 4,192,878, issued Mar. 11, 1980, which is a continuation-in-part of application Ser. No. 836,107, filed Sept. 23, 1977, now abandoned, which is a continuation-in-part of application Ser. No. 747,281, filed Dec. 3, 1976, now abandoned.

SUMMARY OF THE INVENTION

This invention relates to new thiazolidine-, thiazane- and related carboxylic acids which have the general formula

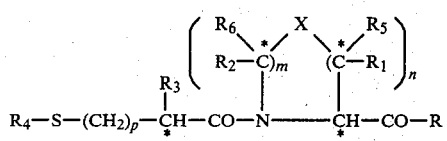

and salts thereof, wherein
R is hydroxy or lower alkoxy;
$R_1$, $R_2$, $R_5$ and $R_6$ each is hydrogen or lower alkyl;
$R_3$ is hydrogen, lower alkyl or mercapto-lower alkylene;
$R_4$ is hydrogen, lower alkanoyl, benzoyl or

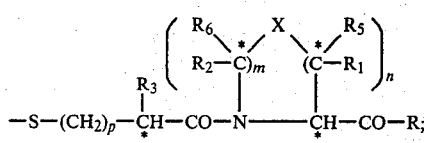

X is O, S, SO or $SO_2$; when X is O, m is 2 and n is 1; m is 1, 2 or 3; n is 0, 1 or 2; and m+n is 2 or 3; p is 0 or 1.
The asterisks denote centers of asymmetry.

DETAILED DESCRIPTION OF THE INVENTION

The invention in its broad aspects includes derivatives of thiazolidine-, thiazane- and related carboxylic acids having formula I above.

The compounds of this invention are characterized by an unsubstituted or lower alkyl substituted 5- or 6-membered heterocyclic carboxylic acid having one nitrogen atom and one sulfur or oxygen atom in the ring, the remaining members of the ring being carbon, preferably thiazolidine-, thiazane- and morpholine carboxylic acids. The ring, as indicated, contains a hetero atom in addition to the nitrogen, which is oxygen or sulfur and the sulfur can be oxidized to the sulfinyl

or sulfonyl

state. The side chain, attached to the nitrogen of the heterocyclic ring, is an unsubstituted or substituted mercapto-alkanoyl group. The compound can also be a "dimer" wherein the sulfur containing substituted $R_4$ is a similar unit.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The lower alkylene groups are of the same kind also having 1 to 7 carbons. Similarly the lower alkoxy groups are of the same kind with a link to oxygen, for example, methoxy, ethoxy, propoxy, isopropoxy, butoxy, isobutoxy, t-butoxy and the like. The $C_1$–$C_4$ members, especially $C_1$ and $C_2$ members, of all types are preferred. The lower alkanoyl groups are the acyl radicals of the lower (up to 7 carbons) fatty acids, e.g., acetyl, propionyl, butyryl and the like, acetyl being preferred.

The symbols have the foregoing meanings throughout this specification.

Certain modifications of the invention having particular structural features, are preferred over other members of the group. In general, compounds of formula I are preferred wherein R is hydroxy or lower alkoxy especially hydroxy, methoxy or ethoxy; $R_1$, $R_2$, $R_5$ and $R_6$ each is hydrogen or lower alkyl, especially hydrogen, methyl or ethyl, most especially hydrogen; $R_3$ is hydrogen, lower alkyl, especially methyl or ethyl, or mercapto-lower alkylene, especially mercaptomethyl; $R_4$ is hydrogen, lower alkanoyl, especially acetyl, or benzoyl; X is sulfur or oxygen, especially sulfur; m is 1 or 2; n is 1; and p is 0 or 1, especially 1.

In addition, compounds having a five membered ring system are preferred over those having a sixmembered ring. In both 5- and 6-membered ring systems the sulfur containing rings are preferred over those wherein X is oxygen, sulfinyl or sulfonyl in that order. Also, the unsubstituted rings, i.e., wherein $R_1$, $R_2$, $R_5$ and $R_6$ are all hydrogen come first, then those wherein $R_1$ and/or $R_2$ is lower alkyl, especially methyl, and lastly disubstituted rings wherein either $R_1$ and $R_5$ or $R_2$ and $R_6$ are lower alkyl, especially methyl, in order of preference.

Specifically, the especially preferred modifications are those compounds of formula I wherein X is sulfur; R is hydroxy or lower alkoxy, especially hydroxy; $R_1$, $R_2$, $R_5$ and $R_6$ each is hydrogen; $R_3$ is hydrogen or lower alkyl, especially hydrogen or methyl; $R_4$ is hydrogen or lower alkanoyl, especially hydrogen or acetyl; m and n each is 1; and p is 0 or 1, especially 1. After these come the compounds of the same type wherein one or two of $R_1$, $R_2$, $R_5$ and $R_6$ is lower alkyl, especially methyl. Following in order of preference are the six-membered rings having the same substituents.

The products of formula I and the preferred subgroups can be produced by various methods of synthesis.

According to a preferred method, the acid of the formula

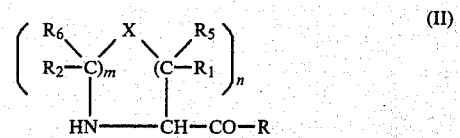

wherein R is hydroxy and the other symbols have the same meaning as above, is acylated with an acid of the formula

by one of the known procedures in which the acid III is activated, prior to reaction with the acid II, involving formation of a mixed anhydride, symmetrical anhydride, acid chloride, active ester, or use of Woodward reagent K, N,N'-carbonylbisimidazole, EEDQ (N-ethoxycarbonyl-2-ethoxy-1,2-dihydroquinoline) or the like. When R is lower alkoxy, this method or other known methods for coupling such moieties can be used. [For review of these methods, see Methoden der Organischen Chemie (Houben-Weyl), Vol. XV, parts 1 and 2 (1974)].

The acid of formula II can, of course, be acylated stagewise. For example, a fragment of the acylating agent III can be first attached to the acid of formula II, e.g., by reacting that acid with a haloacyl halide of the formula

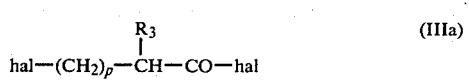

wherein hal represents a halogen, preferably chlorine or bromine, 3-bromopropanoyl chloride for instance. This yields a product of the formula

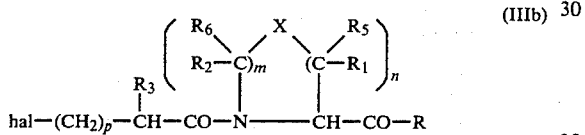

The reaction of this intermediate with a thiol $R_4$—SH then yields the desired product of formula I. This stepwise acylation is illustrated in Example 1.

When the product obtained is an ester, e.g., R is lower alkoxy, the ester can be converted to the free carboxy group by alkaline hydrolysis, or by treatment with trifluoroacetic acid and anisole. Conversely the free acid can be esterified by conventional procedures.

The disulfides, i.e., when $R_4$ is

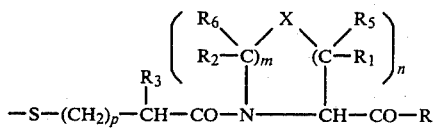

are obtained by oxidation of a compound of the formula

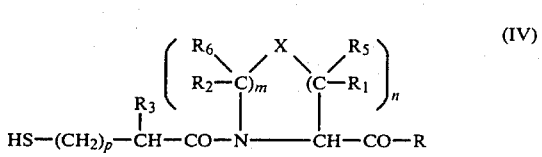

e.g. with an alcoholic solution of iodine.

Products of formula I have at least one or may have up to 4 asymmetric carbon atoms. These carbon atoms are indicated by an asterisk in formula I. The compounds accordingly exist in diastereoisomeric forms or in racemic mixtures thereof. All of these are within the scope of the invention. The above described syntheses can utilize the racemate or one of the enantiomers as starting material. When the racemic starting material is used in the synthetic procedure, the stereoisomers obtained in the product can be separated by conventional chromatographic or fractional crystallization methods. In general, the L-isomer with respect to the carbon of the amino acid constitutes the preferred isomeric form.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product as in the case of the dicyclohexylamine salt.

The salts are formed in conventional manner by reacting the free acid form of the product with one or more equivalents of the appropriate base providing the desired cation in a solvent or medium in which the salt is insoluble and filtering, or in water and removing the water by freeze drying. By neutralizing the salt with an insoluble acid like a cation exchange resin in the hydrogen form [e.g., polystyrene sulfonic acid resin—Dowex 50 (Mikes, Laboratory Handbook of Chromatographic Methods, Van Nostrand, 1961) page 256] or with an aqueous acid and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance present which has been implicated as the causative agent in various forms of hypertension in various mammalian species, e.g., rats, dogs, etc. The compounds of this invention intervene in the angiotensinogen→angiotensin I→angiotensin II sequence by inhibiting angiotensin converting enzyme and reducing or eliminating the formation of the pressor substance angiotensin II.

The inhibition of the angiotensin converting enzyme by compounds of formula I can be measured in vitro with isolated angiotensin converting enzyme from rabbit lungs following the procedure described by Cushman and Cheung [Biochem. Pharmacol., 20, 1637 (1971)], and with an excised smooth muscle assay [E. O'Keefe, et al., Federation Proc. 31, 511 (1972)] in which these compounds have been shown to be powerful inhibitors of the contractile activity of angiotensin I and potentiators of the contractile activity of bradykinin.

The administration of a composition containing one or a combination of compounds of formula I or physiologically acceptable salt thereof to the species of hypertensive mammal alleviates or reduces angiotensin dependent hypertension. A single does, or preferably two to four divided daily doses, provided on a basis of about 5 to 1000 mg. per kilogram per day, preferably about 10 to 500 mg. per kilogram per day is appropriate to reduce blood pressure. The animal model experiments described by S. L. Engel, T. R. Schaeffer, M. H. Waugh and B. Rubin, Proc. Soc. Exp. Biol. Med. 143, 483 (1973) serve as a useful guide.

The substance is preferably administered orally, but parenteral routes such as subcutaneously, intramuscularly, intravenously or intraperitoneally can also be employed.

The compounds of this invention can be utilized to achieve the reduction of blood pressure by formulating in compositions such as tablets, capsules or elixirs for oral administration or in sterile solution or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention and constitute preferred embodiments. All temperatures are in degrees celsius.

EXAMPLE 1

3-(3-Benzoylthiopropanoyl)-4-L-thiazolidinecarboxylic acid

To a solution of L-4-thiazolidinecarboxylic acid (6.6 g.) in normal sodium hydroxide (50 ml.) chilled in an ice bath, 2 N sodium hydroxide (25 ml.) and 3-bromopropanoyl chloride (8.5 g.) are added in that order, with vigorous stirring. After three hours, a suspension of thiobenzoic acid (7.5 g.) and potassium carbonate (4.8 g.) in water (50 ml.) is added. The reaction mixture is stirred overnight at room temperature and filtered. The filtrate is acidified with concentrated hydrochloric acid and extracted with ethyl acetate. The organic layer is dried and concentrated to dryness. The residue is purified by silica gel chromatography (benzene:acetic acid, 7:1) and the purified material is crystallized from ethyl acetate-ether hexane to obtain 3-(3-benzoylthiopropanoyl)-4-L-thiazolidinecarboxylic acid, m.p. 105°–106°.

The above product is dissolved in water and an equivalent proportion of sodium hydroxide solution is added. The solution is then freeze dried to obtain the sodium salt.

EXAMPLE 2

3-(3-Mercaptopropanoyl)-L-4-thiazolidinecarboxylic Acid 3-(3-Benzoylthiopropanoyl)-L-4-thiazolidinecarboxylic acid (6.7 g.) is dissolved in a mixture of water (15 ml.) and concentrated ammonia (7.5 ml.) under a blanket of argon. After one hour storage at room temperature, the reaction mixture is diluted with water (20 ml.) and filtered. The filtrate is extracted with ethyl acetate, acidified with concentrated hydrochloric acid and reextracted with ethyl acetate. The second ethyl acetate extract is dried and concentrated to dryness. The residue, 3-(3-mercaptopropanoyl)-L-4-thiazolidinecarboxylic acid is crystallized from ethyl acetate, m.p. 110°–112°.

EXAMPLE 3

3-Acetylthio-2-methylpropanoic acid

A mixture of thioacetic acid (50 g.) and methacrylic acid (40.7 g.) is heated on the steam bath for one hour and then stored at room temperature for eighteen hours. The reaction mixture is distilled in vacuo and the fraction of b.p. 2.6 mm 128.5°–131° is collected.

The 3-acetylthio-2-methylpropanoic acid can also be isolated by allowing the reaction mixture to crystallize after dilution with hexane, m.p. 40°–42°.

EXAMPLE 4

3-(3-Acetylthio-2-methylpropanoyl)-2-thiazolidinecarboxylic acid methyl ester

2-Thiazolidinecarboxylic acid methyl ester (C.A. 53, 12, 281) (4.4 g.) and 3-hydroxybenzotriazole (4.0 g.) are dissolved in dichloromethane (40 ml.) and the solution is stirred and chilled in an ice bath. Dicyclohexylcarbodiimide (6.2 g.) dissolved in dichloromethane (15 ml.) is added followed immediately by a solution of 3-acetylthio-2-methylpropanoic acid (4.9 g.) in dichloromethane (5 ml.). After fifteen minutes stirring in the ice bath, and sixteen hours at room temperature, the precipitate is filtered off and the filtrate is washed neutral. The organic layer is dried and concentrated to dryness in vacuo to give 3-(3-acetylthio-2-methylpropanoyl)-2-thiazolidinecarboxylic acid methyl ester.

EXAMPLE 5

3-(3-Mercapto-2-methylpropanoyl)-2-thiazolidinecarboxylic acid 3-(3-Acetylthio-2-methylpropanoyl)-2-thiazolidinecarboxylic acid methyl ester (2.9 g.) is dissolved in methanol (30 ml.) and N sodium hydroxide (30 ml.) is added. The reaction mixture is stirred at rooom temperature, aliquots are withdrawn every hour and checked by paper electrophoresis for the hydrolysis of the methyl ester. When this hydrolysis is completed (ca. three hours), the reaction mixture is neutralized, concentrated in vacuo to eliminate methanol, acidified with concentrated hydrochloric acid and extracted with ethyl acetate. The organic layer is dried and concentrated to dryness to yield 3-(3-mercapto-2-methylpropanoyl)-2-thiazolidinecarboxylic acid.

EXAMPLE 6

3-(3-Acetylthio-2-methylpropanoyl)-2-ethyl-4-thiazolidinecarboxylic acid

3-Acetylthio-2-methylpropanoic acid chloride (5.4 g. prepared from 3-acetylthio-2-methylpropanoic acid and thionyl chloride, b.p. 80°) and 2 N sodium hydroxide (15 ml.) are added to a solution of 2-ethyl-4-thiazolidinecarboxylic acid [Z. Naturforschg, 17b, 765 (1962)] (5.2 g.) in normal sodium hydroxide (30 ml.) chilled in an ice-water bath. After three hours stirring at room temperature, the mixture is extracted with ether, the aqueous phase is acidified and extracted with ethyl acetate. The organic phase is dried over magnesium sulfate and concentrated to dryness in vacuo to yield 3-(3-acetylthio-2-methylpropanoyl)-2-ethyl-4-thiazolidinecarboxylic acid.

EXAMPLE 7

2-Ethyl-3-(3-mercapto-2-methylpropanoyl)-4-thiazolidinecarboxylic acid 3-(3-Acetylthio-2-methylpropanoyl)-2-ethyl-4-thiazolidinecarboxylic acid (1 g.) is dissolved in a mixture of water (3 ml.) and concentrated ammonia (3 ml.) under a blanket of argon. The mixture is stirred at room temperature for thirty minutes and acidified with concentrated hydrochloric acid. The organic layer is dried and concentrated to dryness in vacuo to yield 2-ethyl-3-(3-mercapto-2-methylpropanoyl)-4-thiazolidinecarboxylic acid.

EXAMPLE 8

3-(3-Mercapto-2-methylpropanoyl)-5-methyl-4-thiazolidinecarboxylic acid

By substituting 5-methyl-4-thiazolidinecarboxylic acid [Org. Mag. Resonance, 6 48 (1974)] for the ethyl-4-thiazolidinecarboxylic acid in the procedure of Example 6 and then submitting the product to the procedure of Example 7, 3-(acetylthio-2-methylpropanoyl)-5-methyl-4-thiazolidinecarboxylic acid and 3-(3-mercapto-2-methylpropanoyl)-5-methyl-4-thiazolidinecarboxylic acid are obtained.

EXAMPLE 9

3-[(2-Acetylthiomethyl)-3-acetylthiopropanoyl]-4-L-thiazolidinecarboxylic acid

To a solution of 4-L-thiazolidinecarboxylic acid (1.66 g.) and sodium carbonate (2.7 g.) in water (25 ml.) in an ice bath, 2-(acetylthiomethyl)-3-acetylthiopropanoic acid chloride [3.9 g. prepared from 2-acetylthiomethyl)-3-acetylthiopropanoic acid and thionyl chloride] is added and the mixture is vigorously stirred at room temperature for two hours. After extraction with ethyl acetate, the aqueous layer is acidified and extracted with ethyl acetate. The organic layer is dried and concentrated to dryness to yield 3-[(2-acetylthiomethyl)-3-acetylthiopropanoyl]-4-L-thiazolidinecarboxylic acid.

EXAMPLE 10

3-[(2-Mercaptomethyl)-3-mercaptopropanoyl]-4-L-thiazolidinecarboxylic acid

By substituting 3-[(2-acetylthiomethyl)-3-acetylthiopropanoyl]-4-L-thiazolidinecarboxylic acid for 3-(3-acetylthio-2-methylpropanoyl)-2-ethyl-4-thiazolidinecarboxylic acid in the procedure of Example 7, 3-[(2-mercaptomethyl)-3-mercaptopropanoyl]-4-L-thiazolidinecarboxylic acid is obtained.

EXAMPLE 11

3-(3-Mercaptopropanoyl)-1,3-thiazane-4-carboxylic acid

By substituting 1,3-thiazane-4-carboxylic acid [J. Biol. Chem., 607 (1957)] for 4-L-thiazolidinecarboxylic acid in the procedure of Example 1 and then submitting the product to the procedure of Example 2, 3-(3-benzoylthiopropanoyl)-1,3-thiazone-4-carboxylic acid and 3-(3-mercaptopropanoyl)-1,3-thiazane-4-carboxylic acid are obtained.

EXAMPLE 12

3-(3-Mercapto-2-methylpropanoyl)-1,3-thiazane-4-carboxylic acid

By substituting 1,3-thiazane-4-carboxylic acid for the 2-ethyl-4-thiazolidinecarboxylic acid in the procedure of Example 6, and then submitting the product to the procedure of Example 7, 3-(3-acetylthio-2-methylpropanoyl)-1,3-thiazane-4-carboxylic acid and 3-(3-mercapto-2-methyl-propanoyl)-1,3-thiazane-4-carboxylic acid are obtained.

EXAMPLE 13

3-[(2-Mercaptomethyl)-3-mercaptopropanoyl]-1,3-thiazane-4-carboxylic acid

By substituting 1,3-thiazane-4-carboxylic acid for the 4-thiazolidinecarboxylic acid in the procedure of Example 9, and then submitting the product to the procedure of Example 7, 3-[(2-acetylthiomethyl)-3-acetylthiopropanoyl]-1,3-thiazane-4-carboxylic acid and 3-[(2-mercaptomethyl)-3-mercaptopropanoyl]-1,3-thiazane-4-carboxylic acid are obtained.

EXAMPLE 14

4-(3-Acetylthiopropanoyl)-3-methyl-1,4-thiazane-5-carboxylic acid

3-Acetylthiopropanoyl chloride (8.3 g.) is added to a mixture of 3-methyl-1,4-thiazane-5-carboxylic acid [Acta. Chem. Scand. 13, 623 (1959)] (8 g.) in dimethylacetamide while keeping the temperature below 25°. N-Methylmorpholine (10.1 g.) is added and the mixture is heated on the steam bath for one hour. After cooling to room temperature the precipitate formed is filtered and the filtrate is concentrated to dryness in vacuo. The residue is dissolved in ethyl acetate and washed with 10% potassium bisulfate. The organic layer is dried and concentrated to dryness to yield 4-(3-acetylthiopropanoyl)-3-methyl-1,4-thiazine-5-carboxylic acid.

EXAMPLE 15

4-(3-Mercaptopropanoyl)-3-methyl-1,4-thiazane-5-carboxylic acid

By substituting 4-(3-acetylthiopropanoyl)-3-methyl-1,4-thiazane-5-carboxylic acid for the 3-(3-acetylthio-2-methylpropanoyl)-2-ethyl-4-thiazolidinecarboxylic acid in the procedure of Example 7, 4-(3-mercaptopropanoyl)-3-methyl-1,4-thiazane-5-carboxylic acid is obtained.

EXAMPLE 16

4-(3-Mercapto-2-methylpropanoyl)-3-methyl-1,4-thiazane-5-carboxylic acid

By substituting 3-acetylthio-2-methylpropanoyl chloride for the 3-acetylthiopropanoyl chloride in the procedure of Example 14, and then submitting the product to the procedure of Example 7, 4-(3-acetylthio-2-methylpropanoyl)-3-methyl-1,4-thiazane-5-carboxylic acid and 4-(3-mercapto-2-methylpropanoyl)-3-methyl-1,4-thiazane-5-carboxylic acid are obtained.

EXAMPLE 17

4-[(2-Mercaptomethyl)-3-mercaptopropanoyl]-3-methyl-1,4-thiazane-5-carboxylic acid By substituting 2-(acetylthiomethyl)-3-acethylthiopropanoic acid chloride for the 3-acetylthiopropanoyl chloride in the procedure of Example 14, and then submitting the product to the procedure of Example 7, 4-[(2-acetylthiomethyl)-3-(acetylthio)propanoyl]-3-methyl-1,4-thiazane-5-carboxylic acid, and 4-[(2-mercaptomethyl)-3-mercaptopropanoyl]-3-methyl-1,4-thiazane-5-carboxylic acid are obtained.

EXAMPLE 18

4-(3-Mercapto-2-methylpropanoyl)-1-oxo-1,4-L-thiazane-5-carboxylic acid

By substituting 3-acetylthio-2-methylpropanoyl chloride for the 3-acetylthiopropanoyl chloride and 1-oxo-1,4-thiazane-5-carboxylic acid [C.A., 55, 95801] for the 3-methyl-1,4-thiazane-5-carboxylic acid in the procedure of Example 14, and then submitting the product to the procedure of Example 7, 4-(3-acetylthio-2-methylpropanoyl)-1-oxo-1,4-L-thiazane-5-carboxylic acid and 4-(3-mercapto-2-methylpropanoyl)-1-oxo-1,4-L-thiazane-5-carboxylic acid are obtained.

EXAMPLE 19

Ethyl-4-[(3-acetylthio)-2-methylpropanoyl]-1,4-thiazane-3-carboxylate

By substituting ethyl 1,4-thiazane-3-carboxylate [J. Chem. Soc., 203 (1976)] for 2-thiazolidinecarboxylic acid methyl ester in the procedure of Example 4, ethyl-4-[(3-acetylthio)-2-methylpropanoyl]-1,4-thiazane-3-carboxylate is obtained.

EXAMPLE 20

4-(3-Mercapto-2-methylpropanoyl)-1,4-thiazane-3-carboxylic acid

By substituting ethyl 4-[(3-acetylthio)-2-methylpropanoyl]-1,4-thiazane-3-carboxylate for the 3-(3-acetylthio-2-methylpropanoyl)-2-thiazolidine carboxylic acid methyl ester in the procedure of Example 5, 4-(3-mercapto-2-methylpropanoyl)-1,4-thiazane-3-carboxylic acid is obtained.

EXAMPLE 21

N-[(2-Acetylthiomethyl)-3-(acetylthio)propanoyl]-3-morpholinecarboxylic acid

By substituting 3-morpholinecarboxylic acid for the 4-thiazolidinecarboxylic acid in the procedure of Example 9, N-[(2-acetylthiomethyl)-3-(acetylthio)propanoyl]-3-morpholinecarboxylic acid is obtained.

EXAMPLE 22

N-[(2-Mercaptomethyl)-3-mercaptopropanoyl]-3-morpholinecarboxylic acid

By substituting N-[(2-acetylthiomethyl)-3-(acetylthio)propanoyl]-3-morpholinecarboxylic acid for the 3-[(2-acetylthiomethyl)-3-(acetylthio)propanoyl]-4-L-thiazolidinecarboxylic acid in the procedure of Example 1, N-[(2-mercaptomethyl)-3-mercaptopropanoyl]-3-morpholinecarboxylic acid is obtained.

EXAMPLE 23

3-(2-Benzoylthiopropanoyl)-4-L-thiazolidinecarboxylic acid

By substituting 2-bromopropionyl chloride for the 3-bromopropionyl chloride in the procedure of Example 1, 3-(2-benzoylthiopropanoyl)-4-L-thiazolidinecarboxylic acid is obtained.

EXAMPLE 24

3-(2-Mercaptopropanoyl)-4-L-thiazolidinecarboxylic acid

By substituting 3-(2-benzoylthiopropanoyl)-4-L-thiazolidinecarboxylic acid for the 3-(3-benzoylthiopropanoyl)-4-L-thiazolidinecarboxylic acid in the procedure of Example 2, 3-(2-mercaptopropanoyl)-4-L-thiazolidinecarboxylic acid is obtained.

EXAMPLE 25

3,3'-[Dithiobis-(3-propanoyl)]bis-L-thiazolidine-4-carboxylic acid

An alcoholic solution of iodine is added to an equimolar aqueous mixture of 3-(3-mercaptopropanoyl)-L-thiazolidine-4-carboxylic acid until persistent yellow color, while maintaining the pH between 5 and 7 by careful addition of N sodium hydroxide. The yellow color is discharged with a few drops of sodium thiosulfate and the mixture is acidified with concentrated hydrochloric acid and extracted with ethyl acetate. The organic layer is dried and concentrated to dryness in vacuo to yield 3,3'-[dithiobis-(3-propanoyl)]bis-L-thiazolidine-4-carboxylic acid.

EXAMPLE 26

1,1-Dioxo-3-methyl-1,4-thiazane-5-carboxylic acid

A solution of 3-methyl-1,4-thiazane-5-carboxylic acid (6 g.) in acetic acid (300 ml.) is stirred at 45° for 6 hours while 30% hydrogen peroxide (25 ml.) is added at a rate of 5 ml/liter. The solution is set aside overnight and the solvent is removed in vacuo to yield 1,1-dioxo-3-methyl-1,4-thiazane-5-carboxylic acid.

EXAMPLE 27

1,1-Dioxo-4-(3-mercapto-2-methylpropanoyl)-3-methyl-1,4-thiazane-5-carboxylic acid By substituting 1,1-dioxo-3-methyl-1,4-thiazane-5-carboxylic acid for the 3-methyl-1,4-thiazane-5-carboxylic acid in the procedure of Example 16 and then submitting the product to the procedure of Example 7, 1,1-dioxo-4-(3-acetylthio-2-methylpropanoyl)-3-methyl-1,4-thiazane-5-carboxylic acid and 1,1-dioxo-4-(3-mercapto-2-methylpropanoyl)-3-methyl-1,4-thiazane-5-carboxylic acid are obtained.

EXAMPLE 28

3-(3-Mercapto-2-methylpropanoyl)-L-4-thiazolidinecarboxylic acid

By substituting L-4-thiazolidinecarboxylic acid for the 2-ethyl-3-thiazolidinecarboxylic acid in the procedure of Example 6, and then submitting the product to the procedure of Example 7, 3-(3-acetylthio-2-methylpropanoyl)-L-4-thiazolodinecarboxylic acid [dicyclohexylamine salt crystallized from acetonitrile, m.p. 172°–186° (sint. 130°)] and 3-(3-mercapto-2-methylpropanoyl)-L-4-thiazolidinecarboxylic acid [dicyclohexylamine salt crystallized from ethyl acetate/hexane, 180°–188° (sint. 170°)] are obtained.

EXAMPLE 29

3,3'-[Dithiobis-(2-methyl-3-propanoyl)]bis-thiazolidine-2-carboxylic acid

By substituting 3-(3-mercapto-2-methylpropanoyl)-thiazolidine-2-carboxylic acid for the 3-(3-mercaptopropanoyl)-L-thiazolidine-4-carboxylic acid in the procedure of Example 25, 3,3'-[dithiobis-(2-methyl-3-propanoyl)]bisthiazolidine-2-carboxylic acid is obtained.

EXAMPLE 30

4-(3-Acetylthiopropanoyl)-L-1,4-thiazane-5-carboxylic acid

L-4-thiomorpholine-3-carboxylic acid hydrochloride (6.6 g., 0.036 m) is dissolved in 150 ml. dimethylacetamide and 3-acetylthiopropanoyl chloride (5.97 g., 0.036 m) is added. The temperature rises to 28°. To this solution is added N-methylmorpholine (10.9 g., 0.108 m). The temperature rises to 42° and a white precipitate forms immediately. The mixture is heated on a steam bath for one hour and allowed to stand overnight at room temperature. The solid is filtered off to yield 9.7 g. of 4-(3-acetylthiopropanoyl)-L-1,4-thiazane-5-carboxylic acid, m.p. 202°–204°. The solvent is removed to yield a viscous residue which is triturated with water and 20% hydrochloric acid. The precipitated oil is extracted with $3 \times 150$ ml. of ethyl acetate and the extracts are dried over magnesium sulfate. The solvent is removed and the viscous residue (7.5 g.) crystallizes on standing. After recrystallizing from acetone-hexane, the product is constant melting at 122°–125°.

EXAMPLE 31

4-(3-Mercaptopropanoyl)-L-1,4-thiazane-5-carboxylic acid

Aqueous ammonia (13 ml. conc. ammonium hydroxide in 30 ml. of water) is stirred under nitrogen for 15 minutes and solid 4-(3-acetylthiopropanoyl)-L-1,4-thiazane-5-carboxylic acid (6.8 g., 0.024 m) is added. A clear solution forms promptly at 5°–10°. The solution is stirred at room temperature under nitrogen for one hour. The solution is extracted with 100 ml. of ethyl acetate and the aqueous layer is made strongly acid with 20% hydrochloric acid. The precipitated oil is extracted with $3 \times 150$ ml. of ethyl acetate. The extracts are combined and dried over magnesium sulfate, then the solvent is removed to yield 5.6 g. of semicrystalline mass which appears to contain an appreciable amount of starting material. The recovered material (5.6 g.) is hydrolyzed again as above with 12 ml. of concentrated ammonium hydroxide in 25 ml. of water for an additional two hours. This solution is acidified and the precipitated oil is extracted with $3 \times 150$ ml. of ethyl acetate. The extracts are combined and dried over magnesium sulfate, then the solvent is removed to yield 2.7 g. (48%) of 4-(3-mercaptopropanoyl)-L-1,4-thiazane-5-carboxylic acid as a viscous mass after drying overnight at room temperature and 1 mm.

Anal. calcd. for $C_8H_{13}NO_3S_2$: N, 5.95; C, 40.82; H, 5.56; S, 27.25; SH, 100%. Found: N, 6.13; C, 40.85; H, 5.46; S, 27.38; SH, 96%.

EXAMPLE 32

3-(3-Acetylthiopropanoyl)-2,2-dimethyl-4-L-thiazolidinecarboxylic acid 2,2-Dimethylthiazolidine-4-carboxylic acid (5.74 g.) is dissolved in 58 ml. of anhydrous pyridine with heating. The solution is chilled in an ice bath with stirring and 3-acetylthiopropanoyl chloride (4.814 g.) is added dropwise. The bath is removed and the reaction mixture is kept overnight at room temperature. The precipitate is filtered and the filtrate is concentrated to dryness in vacuo. The residue is taken up into ethyl acetate, washed with potassium bisulfate and water. The ethyl acetate extract is dried over magnesium sulfate and concentrated to dryness in vacuo. This residue is triturated with ether, filtered and the filtrate is concentrated to dryness, then crystallized from acetonitrile to yield 2.63 g. of 3-(3-acetylthiopropanoyl)-2,2-dimethyl-4-L-thiazolidinecarboxylic acid, m.p., 126°–127°.

EXAMPLE 33

3-(3-Mercaptopropanoyl)-2,2-dimethyl-4-L-thiazolidinecarboxylic acid 3-(Acetylthiopropanoyl)-2,2-dimethyl-4-L-thiazolidinecarboxylic acid (5.82 g.) is dissolved in a cold solution of 15 ml. of water and 15 ml. of concentrated ammonium hydroxide under argon and kept for thirty minutes at room temperature. The reaction mixture is chilled and acidified with concentrated hydrochloric acid. The crystals are chilled, filtered and washed with water, yield 4.79 g., m.p. 132°–136° (haze). This is taken up in hot acetonitrile and the haze filtered. The filtrate yields 3.4 g. of 3-(3-mercaptopropanoyl)-2,2-dimethyl-4-L-thiazolidinecarboxylic acid, m.p., 135°–136°.

EXAMPLE 34

3-(D-3-Acetylthio-2-methylpropanoyl)-2,2-dimethyl-4-L-thiazolidinecarboxylic acid 2,2-Dimethyl-4-thiazolidinecarboxylic acid hydrochloride (19.8 g.) is dissolved in 200 ml. of anhydrous pyridine with stirring in an ice bath. To this 3-acetylthio-2-methylpropanoyl chloride (18.0 g.) is added dropwise. The reaction mixture is stirred overnight at room temperature. The precipitate is filtered and the filtrate concentrated to dryness in vacuo. The residue is dissolved in ethyl acetate, washed with 10% potassium bisulfate, water, dried over magnesium sulfate and concentrated to dryness in vacuo to obtain 31 g. of crude 3-(D-3-acetylthio-2-methylpropanoyl)-2,2-dimethyl-4-L-thiazolidinecarboxylic acid. The dicyclohexylamine salt is obtained by adding the free acid and dicyclohexylamine to acetonitrile, yield 24 g. The dicyclohexylamine salt is recrystallized from 700 ml. of acetonitrile to yield 18.2 g., m.p. 197°–198°. The salt is converted back to the free acid by dissolving in ethyl acetate and 10% of potassium bisulfate then crystallizing from 100 ml. of acetonitrile to yield 8.9 g., m.p. 171°–172°.

EXAMPLE 35

3-(L-3-Acetylthio-2-methylpropanoyl)-2,2-dimethyl-4-L-thiazolidinecarboxylic acid The mother liquors from the preparation of the dicyclohexylamine salt obtained in Example 34 are concentrated to dryness in vacuo. The residue is added to ethyl acetate and 10% potassium bisulfate, then crystallized from 80 ml. of acetonitrile to obtain 7.5 g. of 3-(L-3-acetylthio-2-methylpropanoyl)-2,2-dimethyl-4-L-thiazolidinecarboxylic acid.

EXAMPLE 36

3-(D-3-Mercapto-2-methylpropanoyl)-2,2-dimethyl-4-L-thiazolidinecarboxylic acid 3-(D-3-Acetylthio-2-methylpropanoyl)-2,2-dimethyl-L-thiazolidinecarboxylic acid, (5 g.) is dissolved in a cold solution of 15 ml. of water and 15 ml. of concentrated ammonium hydroxide while under a blanket of argon. After thirty minutes, it is chilled and acidified with concentrated hydrochloric acid. The crystalline precipitate is filtered and washed with water. The product 3-(D-3-mercapto-2-methylpropanoyl)-2,2-dimethyl-4-L-thiazolidinecarboxylic acid is recrystallized from 40 ml. of acetonitrile (haze filtered), yield 4.2 g., m.p. 174°–175°.

EXAMPLE 37

3-(L-3-Mercapto-2-methylpropanoyl)-2,2-dimethyl-4-L-thiazolidinecarboxylic acid 3-(L-3-Acetylthio-2-methylpropanoyl)-2,2-dimethyl-4-L-thiazolidinecarboxylic acid, (4 g.) is dissolved in a cold solution of 6 ml. of water and 6 ml. of concentrated ammonium hydroxide under an argon blanket. After thirty minutes at room temperature, it is chilled and acidified with concentrated hydrochloric acid. The crystalline precipitate is filtered and washed with water. The product, 3-(L-3-mercapto-2-methylpropanoyl)-2,2-dimethyl-4-L-thiazolidinecarboxylic acid is recrystallized from acetonitrile (insoluble filtered), yield 3.7 g., m.p. 197°–198°.

EXAMPLE 38

3-(3-Acetylthiopropanoyl)-5,5-dimethyl-4-DL-thiazolidinecarboxylic acid (a) 5,5-Dimethyl-4-thiazolidinecarboxylic acid DL-Penicillamine (20 g., 134 mmol.) is dissolved in 134 ml. of 1 N hydrochloric acid at room temperature, and 40 ml. (492 mmol.) of 37% aqueous formaldehyde are added. After thirty minutes, sodium acetate (11 g., 134 mmol.) is added, and the reaction mixture is stirred at room temperature overnight. After filtering, the solid is washed with ice cold 50% aqueous ethanol, and dried in vacuo to yield 14.4 g. of the product, 5,5-dimethyl-4-thiazolidinecarboxylic acid, m.p. 209°–210°. After concentrating in vacuo, the mother liquor is triturated with 95% ethanol to afford an additional 1.4 g. of product, m.p. 212°–213°, total yield 15.8 g. (73%).

(b) [3-(3-Acetylthiopropanoyl)]-5,5-dimethyl-4-DL-thiazolidinecarboxylic acid

The product of part a (6 g., 37.2 mmol.) is dissolved in a mixture of 3.5 g. (41.4 mmol.) of sodium bicarbonate in 42 ml. of tetrahydrofuran and 41 ml. of water. 3-(Acetylthiopropanoyl)chloride (5.5 ml., 41.1 mmol.) in 5.5 ml. of ether is added dropwise followed by titration with 2 N sodium hydroxide, keeping the pH between 6 and 7. The reaction is stirred for thirty minutes after completion of the addition, then quenched with 100 ml. of 1 N hydrochloric acid. The mixture is extracted with 2×250 ml. of ethyl acetate and the organic extracts are washed with 100 ml. portions of water and brine, dried ($Na_2SO_4$), and stripped to dryness in vacuo. The resulting oil solidifies upon standing at room temperature to yield 11.0 g. of crude [3-(3-acetylthiopropanoyl)]-5,5-dimethyl-4-DL-thiazolidinecarboxylic acid. Recrystallization from ether/petroleum ether gives 7.9 g. (73%) of product, m.p. 99°–100.5°.

EXAMPLE 39

3-(2-Mercaptoacetyl)-4-L-thiazolidinecarboxylic acid

By substituting chloroacetyl chloride for the 3-bromopropanoyl chloride in the procedure of Example 1 and then proceeding as in Example 2, 3-(2-benzoylthioacetyl)-4-L-thiazolidinecarboxylic acid and 3-(2-mercaptoacetyl)-4-L-thiazolidinecarboxylic acid, respectively, are obtained.

EXAMPLE 40

3-(3-Mercaptopropanoyl)-5,5-dimethyl-4-DL-thiazolidinecarboxylic acid

A suspension of 2.91 g. (10 mmol.) of 3-(3-acetylthiopropanoyl)-5,5-dimethyl-4-thiazolidinecarboxylic acid in 8 ml. of water is stirred rapidly at room temperature under a blanket of argon. The stirred suspension is treated with 8 ml. of ca. 58% aqueous ammonium hydroxide, added dropwise over a period of about one minute. The non-homogeneous solution is stirred under argon for thirty minutes, then chilled and acidified with concentrated hydrochloric acid. The aqueous solution is extracted with 40 ml. and 30 ml. portions of ethyl acetate. The combined organic solutions are washed with 5 ml. of water, 10 ml. of brine, dried ($Na_2SO_4$) and concentrated in vacuo to 2.74 g. of crude oil. When the oil is treated with ca. 50 ml. of (4:6) ethyl acetate/hexanes, rapid crystallization induced by scratching yields 1.88 g. of a light, white solid 3-(3-mercaptopropanoyl)-5,5-dimethyl-4-DL-thiazolidinecarboxylic acid (75%), m.p. 100°–101.5°. Tlc, $R_f$=0.46 (silica gel; 60:20:6:11, EtOAc:pyridine:MeOH:$H_2O$).

EXAMPLE 41

3-(3-Mercapto-2-methylpropanoyl)-2,2,5,5-tetramethyl-4-DL-thiazolidinecarboxylic acid By substituting 2,2,5,5-tetramethyl-4-thiazolidinecarboxylic acid for the 2,2-dimethyl-4-thiazolidinecarboxylic acid hydrochloride in the procedure of Example 34 and then submitting the product to the procedure of Example 36, 3-[3-(acetylthio)-2-methylpropanoyl]-2,2,5,5-tetramethyl-4-DL-thiazolidinecarboxylic acid and 3-(3-mercapto-2-methylpropanoyl)-2,2,5,5-tetramethyl-4-DL-thiazolidinecarboxylic acid are obtained.

EXAMPLE 42

3-(3-Mercapto-2-methylpropanoyl)-2-ethyl-2-methyl-4-L-thiazolidinecarboxylic acid By substituting 2-ethyl-2-methyl-4-L-thiazolidinecarboxylic acid for the 2,2-dimethyl-4-thiazolidinecarboxylic acid hydrochloride in the procedure of Example 34 and then submitting the product to the procedure of Example 36, 3-[3-(acetylthio)-2-methylpropanoyl]-2-ethyl-2-methyl-4-L-thiazolidinecarboxylic acid and 3-(3-mercapto-2-methylpropanoyl)-2-ethyl-2-methyl-4-L-thiazolidinecarboxylic acid are obtained.

EXAMPLE 43

3-(3-Mercaptopropanoyl)-2-ethyl-5,5-dimethyl-4-DL-thiazolidinecarboxylic acid

By substituting 2-ethyl-5,5-dimethyl-4-DL-thiazolidinecarboxylic acid for the 5,5-dimethyl-4-thiazolidinecarboxylic acid in the procedure of Example 38b and then submitting the product to the procedure of Example 40, 3-[3-(acetylthio)propanoyl]-2-ethyl-5,5-dimethyl-4-DL-thiazolidinecarboxylic acid and 3-(3-mercaptopropanoyl)-2-ethyl-5,5-dimethyl-4-DL-thiazolidinecarboxylic acid are obtained.

EXAMPLE 44

3-[2-(Mercaptomethyl)-3-mercaptopropanoyl]-5,5-dimethyl-4-DL-thiazolidinecarboxylic acid By substituting 5,5-dimethyl-4-DL-thiazolidinecarboxylic acid for the 4-L-thiazolidinecarboxylic acid in the procedure of Example 9 and then submitting the product to the procedure of Example 10, 3-[2-(acetylthiomethyl)-3-acetylthiopropanoyl]-5,5-dimethyl-4-DL-thiazolidinecarboxylic acid and 3-[2-(mercaptomethyl)-3-mercaptopropanoyl]-5,5-dimethyl-4-DL-thiazolidinecarboxylic acid are obtained.

EXAMPLE 45

4-(3-Mercapto-2-methylpropanoyl)-5,5-dimethyl-1,4-L-thiazane-3-carboxylic acid

By substituting 5,5-dimethyl-1,4-L-thiazane-3-carboxylic acid for the 2,2-dimethyl-4-L-thiazolidinecarboxylic acid hydrochloride in the procedure of Example 34 and then submitting the product to the procedure of Example 36, 4-[3-(acetylthio)-2-methylpropanoyl]-5,5-dimethyl-1,4-L-thiazane-3-carboxylic acid and 4-(3-mercapto-2-methylpropanoyl)-5,5-dimethyl-1,4-L-thiazane-3-carboxylic acid are obtained.

EXAMPLE 46

Ethyl-2,2-dimethyl-1,4-DL-thiazane-3-carboxylate

A mixture of DL-penicillamine ethyl ester hydrochloride (0.133 mole) and triethylamine (0.4 mole) in chloroform (200 ml.) is added to a solution of ethylene dibromide (0.133 mole) in chloroform:benzene (3:5; 120 ml.). The mixture is refluxed for one hour and then stirred at room temperature for sixteen hours. The precipitate is filtered off, and the filtrate is concentrated in vacuo and then distilled to give ethyl 2,2-dimethyl-1,4-DL-thiazane-3-carboxylate.

EXAMPLE 47

4-(3-Mercapto-2-methylpropanoyl)-2,2-dimethyl-1,4-DL-thiazane-3-carboxylic acid

By substituting ethyl 2,2-dimethyl-1,4-DL-thiazane-3-carboxylate for the 2-thiazolidinecarboxylic acid methyl ester in the procedure of Example 4, and then submitting the product to the procedure of Example 5, ethyl-4-[3-(acetylthio)-2-methylpropanoyl]-2,2-dimethyl-1,4-DL-thiazane-3-carboxylate and 4-(3-mercapto-2-methylpropanoyl)-2,2-dimethyl-1,4-DL-thiazane-3-carboxylic acid are obtained.

EXAMPLE 48

3,3'-[Dithiobis-(3-propanoyl)]-bis-(2,2-dimethyl)-L-thiazolidine-4-carboxylic acid By substituting 3-(3-mercaptopropanoyl)-2,2-dimethyl-L-thiazolidine-4-carboxylic acid for the 3-(3-mercaptopropanoyl)-L-thiazolidine-4-carboxylic acid in the procedure of Example 25, 3,3'-[Dithiobis-(3-propanoyl)]-bis-(2,2-dimethyl)-L-thiazolidine-4-carboxylic acid is obtained.

EXAMPLE 49

3,3'-[Dithiobis-(2-methyl-3-propanoyl)]-bis-1,3-thiazane-4-carboxylic acid

By substituting 3-(3-mercapto-2-methylpropanoyl)-1,3-thiazane-4-carboxylic acid for the 3-(3-mercaptopropanoyl)-L-thiazolidine-4-carboxylic acid in the procedure of Example 25, 3,3'-[Dithiobis-(2-methyl-3-propanoyl)]-bis-1,3-thiazane-4-carboxylic acid is obtained.

EXAMPLE 50

4,4'-[Dithiobis-(3-propanoyl)]-bis-(3-methyl)-1,4-thiazine-5-carboxylic acid

By substituting 4-(3-mercaptopropanoyl)-3-methyl-1,4-thiazine-5-carboxylic acid for the 3-(3-mercaptopropanoyl)-L-thiazolidine-4-carboxylic acid in the procedure of Example 25, 4,4'-[dithiobis-(3-propanoyl)]-bis-(3-methyl)-1,4-thiazane-5-carboxylic acid is obtained.

EXAMPLE 51

N-(3-Mercaptopropanoyl)-3-morpholinecarboxylic acid

By substituting 3-morpholinecarboxylic acid for the 1,4-thiazolidinecarboxylic acid in the procedure of Example 1, and then submitting the product to the procedure of Example 2, N-(3-benzoylthiopropanoyl)-3-morpholinecarboxylic acid and N-(3-mercaptopropanoyl)-3-morpholinecarboxylic acid are obtained.

EXAMPLE 52

N-(3-Mercapto-2-methylpropanoyl)-3-morpholinecarboxylic acid

By substituting 3-morpholinecarboxylic acid for the 2-ethyl-4-thiazolidinecarboxylic acid in the procedure of Example 6 and then submitting the product to the procedure of Example 7, N-(3-acetylthio-2-methylpropanoyl)-3-morpholinecarboxylic acid, and N-(3-mercapto-2-methylpropanoyl)-3-morpholinecarboxylic acid are obtained.

EXAMPLE 53

N,N'-[Dithiobis-(3-propanoyl)]-bis-3-morpholinecarboxylic acid

By substituting N-(3-mercaptopropanoyl)-3-morpholinecarboxylic acid for the 3-(3-mercaptopropanoyl)-L-thiazolidine-4-carboxylic acid in the procedure of Example 25, N,N'-[dithiobis-(3-propanoyl)]-bis-3-morpholinecarboxylic acid is obtained.

EXAMPLE 54

N,N'-[Dithiobis-(2-methyl-3-propanoyl)]-bis-3-morpholinecarboxylic acid

By substituting N-(3-mercapto-2-methylpropanoyl)-3-morpholinecarboxylic acid for the 3-(3-mercaptopropanoyl)-L-thiazolidine-4-carboxylic acid in the procedure of Example 25, N,N'-[Dithiobis-(2-methyl-3-propanoyl)]-bis-3-morpholinecarboxylic acid is obtained.

EXAMPLE 55

1,1-Dioxo-3-(3-mercapto-2-methylpropanoyl)-L-thiazolidine-4-carboxylic acid

By substituting 3-(3-acetylthio-2-methylpropanoyl)-L-thiazolidine-4-carboxylic acid for the 3-methyl-1,4-thiazane-5-carboxylic acid in the procedure of Example 26, and then submitting the product to the procedure of Example 7, 1,1-dioxo-3-(3-acetylthio-2-methylpropanoyl)-L-thiazolidine-4-carboxylic acid and 1,1-dioxo-3-(3-mercapto-2-methylpropanoyl)-L-thiozolidine-4-carboxylic acid are obtained.

EXAMPLE 56

1-Oxo-3-(3-mercapto-2-methylpropanoyl)-L-thiazolidine-4-carboxylic acid

A solution of 3-(3-acetylthio-2-methylpropanoyl)-L-thiazolidine-4-carboxylic acid (10 g.) in oxygen-free water (1 liter) is covered with argon and stirred at 10°-15° while 30% hydrogen peroxide (10 ml.) is added at the rate of 1.5 ml/hour. The mixture is stirred overnight at room temperature, acidified and extracted with ethyl acetate. The ethyl acetate is concentrated in vacuo to yield 1-oxo-3-(3-acetylthio-2-methylpropanoyl)-L-thiazolidine-4-carboxylic acid, which is then submitted to the procedure of Example 7 to give 1-oxo-3-(3-mercapto-2-methylpropanoyl)-L-thiazolidine-4-carboxylic acid.

EXAMPLE 57

1-Oxo-4-(3-mercapto-2-methylpropanoyl)-5,5-dimethyl-1,4-L-thiazane-3-carboxylic acid By substituting 1-oxo-5,5-dimethyl-1,4-L-thiazane-3-carboxylic acid for the 2,2-dimethyl-4-L-thiazolidinecarboxylic acid in the procedure of Example 34 and then submitting the product to the procedure of Example 36, 1-oxo-4-(3-acetylthio-2-methylpropanoyl)-5,5-dimethyl-1,4-L-thiazane-3-carboxylic acid and 1-oxo-(3-mercapto-2-methylpropanoyl)-5,5-dimethyl-1,4-L-thiazane-3-carboxylic acid are obtained.

EXAMPLE 58

1-Oxo-3-(3-mercapto-2-methylpropanoyl)-1,3-thiazane-4-carboxylic acid

By substituting 3-(3-acetylthio-2-methylpropanoyl)-1,3-thiazane-4-carboxylic acid for the 3-(3-acetylthio-2-methylpropanoyl)-L-thiazolidine-4-carboxylic acid in the procedure of Example 56, 1-oxo-3-(acetylthio-2-methylpropanoyl)-1,3-thiazane-4-carboxylic acid and 1-oxo-3-(3-mercapto-2-methylpropanoyl)-1,3-thiazane-4-carboxylic acid are obtained.

EXAMPLE 59

3-(3-Acetylthiopropanoyl)-2-methyl-4-L-thiazolidinecarboxylic acid

By substituting 2-methyl-4-L-thiazolidinecarboxylic acid for the L-thiazolidinecarboxylic acid and 2-acetylthiopropanoyl chloride for the 2-(acetylthiomethyl)-3-acetylthiopropanoyl chloride in the procedure of Example 9, 3-(3-acetylthiopropanoyl)-2-methyl-4-L-thiazolidinecarboxylic acid is obtained, m.p. 119°-122°.

EXAMPLE 60

3-(3-Mercaptopropanoyl)-2-methyl-4-L-thiazolidinecarboxylic acid

By substituting 3-(3-acetylthiopropanoyl)-2-methyl-4-L-thiazolidinecarboxylic acid for the 3-(3-acetylthio-2-methylpropanoyl)-4-L-thiazolidinecarboxylic acid in the procedure of Example 7, 3-(3-mercaptopropanoyl)-2-methyl-4-L-thiazolidinecarboxylic acid is obtained, m.p. 89°-95°.

EXAMPLE 61

3-(D-3-Acetylthio-2-methylpropanoyl)-L-thiazolidine-4-carboxylic acid

The dicyclohexylammonium salt of 3-(3-acetylthio-2-methylpropanoyl)-L-thiazolidinecarboxylic acid (5.1 g) is refluxed with 250 ml of acetonitrile, chilled, and filtered. This crystalline product is recrystallized from isopropanol to yield 2 g of 3-(D-3-acetylthio-2-methylpropanoyl)-L-thiazolidine-4-carboxylic acid dicyclohexylammonium salt, m.p. 202°-204°, $[\alpha]_D^{24} = -124.5°$ (c=2, methanol). The salt is converted to the free acid by distribution between 10% aqueous potassium bisulfate and ethyl acetate. The organic phase is concentrated to dryness and the residue is crystallized from ethyl acetate-hexane, m.p. 104°-105°, $[\alpha]_D^{24} = -203.6°$ (c=1.0, methanol).

EXAMPLE 62

3-(D-3-Mercapto-2-methylpropanoyl)-L-thiazolidine-4-carboxylic acid

Substituting 3-(D-3-acetylthio-2-methylpropanoyl)-L-thiazolidine-4-carboxylic acid for the 3-(3-acetylthio-2-methylpropanoyl)-2-ethyl-4-thiazolidinecarboxylic acid in the procedure of Example 7, 3-(D-3-mercapto-2-methylpropanoyl)-L-thiazolidine-4-carboxylic acid is obtained, m.p. 111°-113°, $[\alpha]_D^{24} = -173.7°$ (c=1.6, methanol).

The racemic form of the final product in any of the foregoing examples is produced by utilizing the DL-form of the starting amino acid instead of the L-form.

Similarly, the D-form of the final products in any of the foregoing examples is produced by utilizing the D-form of the starting amino acid instead of the L-form.

Additional members of the group can also be produced by substitution of the appropriate starting material in any of the foregoing examples.

EXAMPLE 63

1000 tablets each containing 100 mg. of 3-(3-mercaptopropanoyl)-L-4-thiazolidinecarboxylic acid are produced from the following ingredients:

| | | |
|---|---|---|
| 3-(3-Mercaptopropanoyl-L-4-thiazolidinecarboxylic acid | 100 | g. |
| Corn starch | 50 | g. |
| Gelatin | 7.5 | g. |
| Avicel (microcrystalline cellulose) | 25 | g. |
| Magnesium stearate | 2.5 | g. |

The 3-(3-mercaptopropanoyl)-L-thiazolidinecarboxylic acid and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg. of active ingredient.

EXAMPLE 64

By substituting 100 g. of 3-(3-mercapto-2-methylpropanoyl)-L-4-thiazolidinecarboxylic acid for the 3-(3-mercaptopropanoyl-L-4-thiazolidinecarboxylic acid in Example 63, 1000 tablets each containing 100 mg. of the 3-(3-mercapto-2-methylpropanoyl-L-4-thiazolidinecarboxylic acid are produced.

EXAMPLE 65

1000 tablets each containing 200 mg. of 3-(2-mercaptoacetyl)-4-L-thiazolidinecarboxylic acid are produced from the following ingredients:

| | |
|---|---|
| 3-(2-Mercaptoacetyl)-4-L-thiazolidinecarboxylic acid | 200 g. |

-continued

| Lactose | 100 g. |
| Avicel | 150 g. |
| Corn starch | 50 g. |
| Magnesium stearate | 5 g. |

The 3-(2-mercaptoacetyl)-4-L-thiazolidinecarboxylic acid, lactose and Avicel are admixed, then blended with the corn starch. Magnesium stearate is added. The dry mixture is compressed in a tablet press to form 1000 505 mg. tablets each containing 200 mg. of active ingredient. The tablets are coated with a solution of Methocel E 15 (methyl cellulose) including as a color a lake containing yellow #6.

EXAMPLE 66

Two piece #1 gelatin capsules each containing 250 mg. of 4-(3-mercapto-2-methylpropanoyl)-1,4-thiazine-3-carboxylic acid are filled with a mixture of the following ingredients:

| 4-(3-Mercapto-2-methylpropanoyl)-1,4-thiazane-3-carboxylic acid | 250 mg. |
| Magnesium stearate | 7 mg. |
| USP lactose | 193 mg. |

EXAMPLE 67

An injectable solution is produced as follows:

| 3-(3-mercaptopropanoyl)-L-4-thiazolidinecarboxylic acid | 500 g. |
| Methyl paraben | 5 g. |
| Propyl paraben | 1 g. |
| Sodium chloride | 25 g. |
| Water for injection qs. | 5 l. |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 2 ml. of solution in a concentration of 100 mg. of active ingredient per ml. of solution for injection.

EXAMPLE 68

By substituting 100 g. of 3,3'-[dithiobis(3-propanoyl)]-bis-L-thiazolidine-4-carboxylic acid for the 3-(3-mercaptopropanoyl-L-4-thiazolidinecarboxylic acid in Example 63, 1000 tablets each containing 100 mg. of the 3,3'-[dithiobis(3-propanoyl)]-bis-L-thiazolidine-4-carboxylic acid are produced.

EXAMPLE 69

By substituting 3-(3-mercapto-2-methylpropanoyl)-L-4-thiazolidinecarboxylic acid for the 3-(3-mercaptopropanoyl)-L-4-thiazolidinecarboxylic acid in Example 67 vials each containing 5 ml. of solution in a concentration of 100 mg. of active ingredients per ml. are obtained.

What is claimed is:
1. A compound of the formula

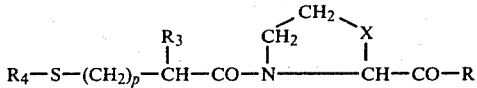

wherein
R is hydroxy or lower alkoxy;
$R_3$ is hydrogen, lower alkyl or mercapto-lower alkylene;
$R_4$ is hydrogen, lower alkanoyl, benzoyl or

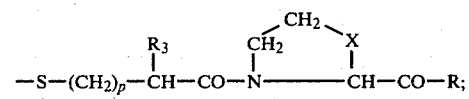

X is S, SO or $SO_2$; and
p is 0 or 1;
or a basic salt thereof; wherein the terms lower alkyl, lower alkoxy and lower alkylene refer to groups having 1 to 7 carbon atoms and the term lower alkanoyl refers to groups having up to 7 carbon atoms; and a pharmaceutically acceptable vehicle therefor.

2. A compound as in claim 1 wherein $R_4$ is hydrogen.
3. A compound as in claim 1 wherein $R_4$ is acetyl.
4. A compound as in claim 1 wherein $R_4$ is benzoyl.
5. A compound as in claim 1 wherein $R_4$ is

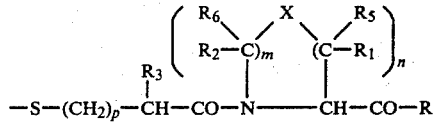

6. A compound as in claim 1 wherein R is hydroxy.
7. A compound as in claim 1 wherein p is 1.
8. A compound as in claim 1 wherein X is sulfur.
9. The compound in accordance with claim 8, 3-(3-acetylthio-2-methylpropanoyl)-2-thiazolidinecarboxylic acid methyl ester.
10. The compound in accordance with claim 8, 3-(3-mercapto-2-methylpropanoyl)-2-thiazolidinecarboxylic acid.
11. The compound in accordance with claim 8, 3,3'-[dithiobis-(2-methyl-3-propanoyl)]bis-thiazolidine-2-carboxylic acid.
12. A composition comprising a compound of the formula

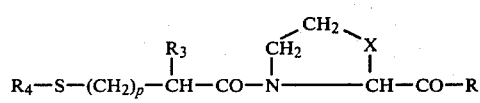

wherein
R is hydroxy or lower alkoxy;
$R_3$ is hydrogen, lower alkyl or mercapto-lower alkylene;
$R_4$ is hydrogen, lower alkanoyl, benzoyl or

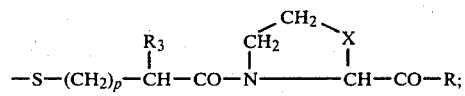

X is S, SO or $SO_2$; and
p is 0 or 1;

or a basic salt thereof; wherein the terms lower alkyl, lower alkoxy and lower alkylene refer to groups having 1 to 7 carbon atoms and the term lower alkanoyl refers to groups having up to 7 carbon atoms; and a pharmaceutically acceptable vehicle therefor.

13. A method for reducing blood pressure which comprises administering a composition comprising a compound of the formula

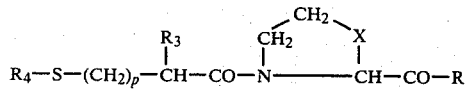

wherein

R is hydroxy or lower alkoxy;

$R_3$ is hydrogen, lower alkyl or mercapto-lower alkylene;

$R_4$ is hydrogen, lower alkanoyl, benzoyl or

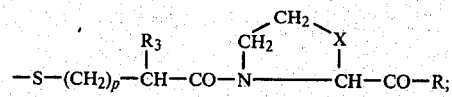

X is S, SO or $SO_2$; and p is 0 or 1;

or a basic salt thereof; wherein the terms lower alkyl, lower alkoxy and lower alkylene refer to groups having 1 to 7 carbon atoms and the term lower alkanoyl refers to groups having up to 7 carbon atoms; and a pharmaceutically acceptable vehicle therefor.

* * * * *

UNITED STATES PATENT AND TRADEMARK OFFICE
CERTIFICATE OF CORRECTION

PATENT NO. : 4,282,235
DATED : August 4, 1981
INVENTOR(S) : Miguel A. Ondetti

It is certified that error appears in the above—identified patent and that said Letters Patent is hereby corrected as shown below:

Column 6, line 21, "12,281)" should read --12,281d)--.

Column 6, line 41, "room" is misspelled.

Column 8, line 40, "thiazane" is misspelled.

Columns 19 and 20, claim 1 should read:

--1. A compound of the formula

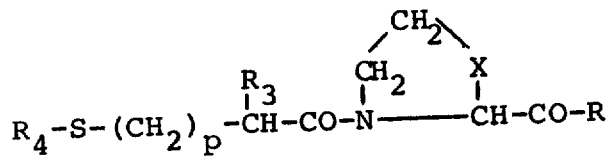

wherein R is hydroxy or lower alkoxy;

$R_3$ is hydrogen, lower alkyl or mercapto-lower alkylene;

$R_4$ is hydrogen, lower alkanoyl, benzoyl or

UNITED STATES PATENT AND TRADEMARK OFFICE
CERTIFICATE OF CORRECTION

PATENT NO. : 4,282,235
DATED : August 4, 1981
INVENTOR(S) : Miguel A. Ondetti

It is certified that error appears in the above—identified patent and that said Letters Patent is hereby corrected as shown below:

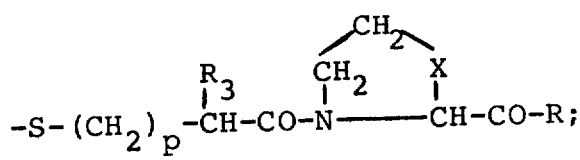

X is S, SO or $SO_2$; and p is 0 or 1;

and basic salts thereof; wherein the terms lower alkyl, lower alkoxy and lower alkylene refer to groups having 1 to 7 carbon atoms and the term lower alkanoyl refers to groups having up to 7 carbon atoms.--

Signed and Sealed this

Eighth Day of December 1981

[SEAL]

Attest:

GERALD J. MOSSINGHOFF

Attesting Officer

Commissioner of Patents and Trademarks